United States Patent [19]

Kastron et al.

[11] 4,219,653
[45] Aug. 26, 1980

[54] 2,6-DIMETHYL-3,5-DIMETHOXYCARBO-NYL-4-(ORTHO-DIFLUOROMETHOXY-PHENYL)-1,4-DIHYDROPYRIDINE

[76] Inventors: Valeria V. Kastron, ulitsa Vaidavas, 7, kv. 43; Rasma O. Vitolin, ulitsa Lielvardes, 26, kv. 39, both of Riga; Jury A. Fialkov, ulitsa Oktyabrskoi Revoljutsii, 13/4, kv. 3; Svetlana V. Shelyazhenko, ulitsa Borschagovskaya, 10-a, kv. 141, both of Kiev; Gunar Y. Dubur, ulitsa Ierikju, 43, kv. 2; Agris A. Kimenis, ulitsa Staitseles, 15, kv. 208, both of Riga; Lev M. Yagupolsky, ulitsa Ivana Kudri, 41, kv. 48, Kiev, all of U.S.S.R.

[21] Appl. No.: 1,148

[22] Filed: Jan. 5, 1979

[30] Foreign Application Priority Data

Jan. 11, 1978 [SU] U.S.S.R. .......................... 2569286[I]

[51] Int. Cl.² .......................................... C07D 213/55
[52] U.S. Cl. ..................................... 546/322; 424/266
[58] Field of Search ........................ 546/322; 424/266

[56] References Cited
U.S. PATENT DOCUMENTS 4,021,434  5/1977  Marakami et al. .................. 546/322

Primary Examiner—Alan L. Rotman
Attorney, Agent, or Firm—J. Harold Nissen

[57] ABSTRACT

The present invention relates to derivatives of 1,4-dihydropyridine and, more specifically, to 2,6-dimethyl-3,5-dimethoxycarbonyl-4-(o-difluoromethoxyphenyl)-1,4-dihydropyridine of the formula:

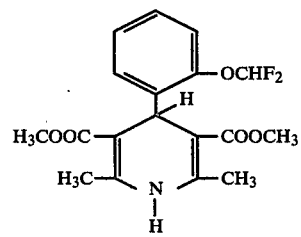

This compound features a clearly pronounced hypotensive activity while being low-toxic, wherefore it can be used in medicine for treating hypertensive disease.

1 Claim, No Drawings

2,6-DIMETHYL-3,5-DIMETHOXYCARBONYL-4-(ORTHO-DIFLUOROMETHOXYPHENYL)-1,4-DIHYDROPYRIDINE

FIELD OF THE INVENTION

The present invention relates to derivatives of 1,4-dihydropyridine and, more specifically, to 2,6-dimethyl-3,5-dimethoxycarbonyl-4-(o-difluoromethoxyphenyl)-1,4-dihydropyridine. Derivatives of 1,4-dihydropyridine possess a pronounced hypotensive activity and can be useful in medicine.

BACKGROUND OF THE INVENTION

Known in the art are a great number of compounds belonging to the series of 1,4-dihydropyridines revealing a hypotensive activity. However, these compounds at the same time have a high toxicity (cf. B. Loev, M. M. Goodman, K. M. Snader, R. Tedeschi, E. Macko, J. Med. Chem., 1974, 17, 956; B. Loev, S. Ehrreich, R. Tedeschi, J. Pharmac., 1972, 24, 917).

Thus, the hypotensive activity of a known compounds, i.e. 2,6-dimethyl-3,5-diethoxycarbonyl-4-(o-trifluoromethylphenyl)-1,4-dihydropyridine (SKF-24260) $ED_{30}=0.022$ mg/kg, but its toxicity is $LD=38.5$ mg/kg. In this connection, considerable efforts are still being made to prepare novel compounds of the series of 1,4-dihydropyridine which would feature lesser toxicity.

OBJECT OF THE INVENTION

It is an object of the present invention to provide such a compound which would have a high hypotensive activity while being low-toxic at the same time.

SUMMARY OF THE INVENTION

In accordance with the present invention, a novel compound is prepared, namely 2,6-dimethyl-3,5-dimethoxycarbonyl-4-(o-difluoromethoxyphenyl)-1,4-dihydropyridine of the formula:

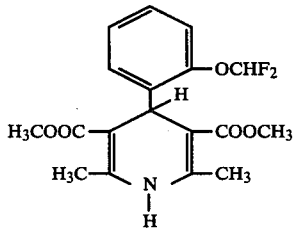

This compound is pharmacologically active. It reveals a highly pronounced hypotensive activity.

The effective dose of this compound making it possible to lower the arterial pressure by 30% is equal to 0.024 mg/kg which is by 10 times higher than the activity of papaverine and is not inferior to the activity of the prior art compound SKF-24260 ($ED_{30}=0.022$ mg/kg). An important advantage of the compound according to the present invention is the fact that it is by 10 times less toxic than said SKF-24260 compound and its antagonism in respect of angiotensin is by 2–3 times higher.

The compound according to the present invention corresponding to the above-given formula can be prepared by condensation of acetoacetic acid methylate, ortho-difluoromethoxybenzaldehyde and ammonia upon heating to reflux in an inert organic solvent. The product comprises a colourless crystalline compound soluble in organic solvents but insoluble in water.

DETAILED DESCRIPTION OF THE INVENTION

The tests for determination of the effect of the novel compound according to the present invention, namely 2,6-dimethyl-3,5-dimethoxycarbonyl-4-(o-difluromethoxy-phenyl)-1,4-dihydropyridine for systemic arterial pressure have been performed on narcotized cats, rats and dogs.

It has been found that the compound according to the present invention, when administered intravenously as a solution in a 50% aqueous dimethylacetamide, causes a clearly pronounced hypotensive effect. Peroral administration of the compound in the form of an aqueous suspension with Twin-80 substantially lowers arterial pressure with rats having artificial hypertonia. As to its hypotensive activity, the compound according to the present invention does not substantially differ from the prior art compound SKF-24260.

Investigating the acute toxicity in tests on white mice upon the intraperitoneal administration of the compound according to the present invention, it has been found that the compound of the present invention is by 10 times less toxic than SKF-24260. The data illustrating hypotensive activity and toxicity of both compounds are shown in Table 1.

In the doses reducing the arterial pressure the compound according to the present invention inhibits hemodynamic effects of biogenic amines such as adrenaline, neoepinephrine, acetylcholine.

Table 1

| Compound | Arterial pressure reducing dose, $ED_{30}$, mg/kg | $LD_{50}$, mg/kg |
|---|---|---|
| The compound of the present invention | 0.024 | 395 |
| The prior art compound SKF-24260 | 0.022 | 38 |

In tests on rats it has been shown that the compound according to the present invention has the same antagonism in respect of noradrenaline as SKF-24260, while its antagonism in respect of angiotensin is substantially more pronounced. The data illustrating antagonism of both compounds are given in Table 2 hereinbelow.

Taking into account the clearly pronounced hypotensive activity for both intravenous and oral administration and a relatively low toxicity of the compound according to the present invention, it can be concluded that the compound of the present invention is of a great practical interest and can be useful for the manufacture of a preparation employed in medical practice for treating hypertensive disease.

Table 2

| Compound | Dose, mg/kg | Relative pressor effect of noradrenaline | Relative pressor effect of angiotension |
|---|---|---|---|
| The compound of the present invention | 0.04 | 0.17 | 0.067 |
| The prior art compound SKF-24260 | 0.04 | 0.23 | 0.16 |

Given hereinbelow is the Example illustrating preparation of 2,6-dimethyl-3,5-dimethoxycarbonyl-4-(o-difluoromethoxyphenyl)-1,4-dihydropyridine.

EXAMPLE 2.40 g (0.0139 mol) of o-difluoromethoxybenzaldehyde, 3.23 g (0.0278 mol) of acetoacetic acid methylate, 5 ml of an aqueous solution of ammonia and 10 ml of methanol are heated at reflux for 3 hours. After cooling and addition of 40 ml of hexane a light-yellow precipitate is formed constituting 2,6-dimethyl-3,5-dimethoxycarbonyl-4-(o-difluoromethoxyphenyl)-1,4-dihydropyridine. After crystallization from methanol there are obtained 2.03 g (40%) of a colourless substance melting at 153°–154° C.; UV-spectrum, $\lambda_{max}$, nm (lg $\epsilon$): 205 (4.36); 243 (4.26), 366 (3.82).

IR-spectrum, $cm^{-1}$: 1619; 1682; 3340.

ESR-spectrum; $\delta$, ppm (in $COCl_3$): 2.22 (6H, c, 2,6-$CH_3$); 3.52 (3H, c, $OCH_3$); 5.19 (IH, c 4-H); 5.75 (1H, c, NH); 6.40 (IH, m, $OCHF_2$); 7.02 (4H, m, aromat.).

Calculated, %: C, 58.8; H, 5.2; N, 3.8. $C_{18}H_{19}F_2NO_5$.
Found, %: C,59.0; H, 5.2; N, 3.7.

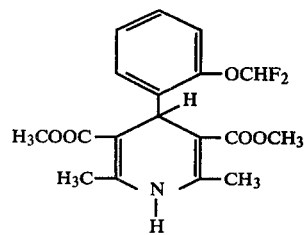

What is claimed is:
1. 2.6-Dimethyl-3,5-dimethoxycarbonyl-4-(o-difluoromethoxyphenyl)-1,4-dihydropyridine of the formula: